US00PP27294P3

(12) United States Plant Patent
Zaiger et al.

(10) Patent No.: US PP27,294 P3
(45) Date of Patent: Oct. 25, 2016

(54) INTERSPECIFIC TREE NAMED 'AMIGO III'

(50) Latin Name: **Interspecific *Prunus* species**
Varietal Denomination: Amigo III

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 131 days.

(21) Appl. No.: 14/544,566

(22) Filed: Jan. 23, 2015

(65) Prior Publication Data

US 2016/0219769 P1 Jul. 28, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Keith Robinson

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Heavy and regular bearer of medium to large size fruit.
3. Fruit with good handling and shipping quality.
4. Fruit with very good flavor and eating quality.
5. Fruit with an average 17.6° Brix.

1 Drawing Sheet

Botanical designation: Interspecific *Prunus* species.
Variety denomination: 'Amigo III'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of interspecific and plum trees, which are known to us, an mentioned herein, 'Flavor Supreme' Interspecific (U.S. Plant Pat. No. 6,763), 'Coparose' Interspecific (U.S. Plant Pat. No. 20,173), our non-patented proprietary interspecific seedlings '66Z68', '44GH13' and our non-patented proprietary plum seedlings '276LF278', '19GF223' and '38RC246'.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species; *Prunus salicina* and *Prunus armeniaca*. The present variety was selected as a first generation cross between our proprietary non-patented plum seedling with the field identification number '276LF278' and our non-patented interspecific seedling '66Z68'. The seed parent '276LF278' (non-patented) plum originated as a first generation cross between our proprietary non-patented plum seedlings '19GF223' and '38RC246'. The interspecific pollen parent '66Z68' (non-patented) originated as a first generation cross between the interspecific 'Flavor Supreme' (U.S. Plant Pat. No. 6,763) and the non-patented interspecific apricot seedling with our field identification number '44GH13'. We budded a large number of these seedlings to older 'Nemaguard' Rootstock (non-patented) trees to induce earlier fruit production for evaluation. Under close and careful observation the present seedling exhibited desirable fruit and tree characteristics and was selected in 2000 for additional asexual propagation and commercialization.

ASEXUAL REPRODUCTION OF THE VARIETY

In 2000 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree, [Plum×((Plum×Plumcot)×(Apricot×Plumcot))] is of large size, vigorous, upright growth and a regular and productive bearer of medium to large size, yellow flesh, clingstone fruit with very good flavor and eating quality. The fruit is further characterized by holding firm on the tree 3 weeks after maturity (shipping ripe) and having good storage and shipping quality. In comparison to its non-patented seed parent ('276LF278') the fruit of the new variety is larger in size. In comparison to its non-patented interspecific pollen parent '66Z68' the fruit of the new variety is larger in size and is approximately 45 days later in maturity. In comparison to the commercial variety 'Coparose' Interspecific (U.S. Plant Pat. No. 20,173) the fruit of the new variety is larger in size and is approximately 10 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 13 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 13 year old specimens grown near Modesto, Calif., with color in accordance with Munsell Book of Color published in 1958.

Tree:

*Size*.—Large, pruned to 3 to 3.5 meters in height and width for economical harvesting of fruit. Size varies with different cultural practices.

*Vigor*.—Vigorous, tree growth of approximately 1.5 to 2 meters the first growing season. Varies with cultural practices, soil type, fertility and climatic conditions.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size. Fruit set varies with climatic conditions during bloom time.

*Bearer*.—Regular, adequate fruit set 11 consecutive years. No alternate bearing observed.

*Fertility*.—Self-sterile, pollinator required.

*Density*.—Medium dense, usually pruned to vase shape to increase sunlight and air movement to center of tree to enhance fruit quality and health of fruit spurs.

*Hardiness*.—Hardy in all stone fruit growing areas of California. Tree grown in USDA Hardiness Zone 9. Winter chilling requirement approximately 650 hours at or below 45° F.

Trunk:

*Size*.—Large. Average circumference 66.7 cm at 28.0 cm above ground on a 10 year old tree.

*Stocky*.—Medium stocky.

*Texture*.—Medium shaggy, roughness increases with age.

*Color*.—Varies from 5Y 4/2 to 5Y 3/2.

Branches:

*Size*.—Large. Average circumference 16.3 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 37 in a 25.8 sq cm section. Average length 4.8 mm. Average width 2.8 mm. Color varies from 7.5YR 6/8 to 7.5YR 5/10.

*Color*.—New growth varies from 2.5GY 5/8 to 7.5R 3/4. Mature growth varies from 10YR 2/2 to 2.5Y 2/2, varies with age of growth.

Leaves:

*Size*.—Medium. Average length 109.4 mm. Average width 44.0 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Medium. Average length 13.4 mm. Average width 1.4 mm. Longitudinally grooved. Surface-light pubescence. Color varies from 5GY 6/6 to 5GY 5/6.

*Glands*.—Type — globose. Number varies from 1 to 5, average number 3. Average length 0.7 mm. Average width 0.5 mm. Located primarily on the upper portion of petiole and the base of the leaf blade. Color varies from 2.5GY 6/6 to 5GY 6/6.

*Stipules*.—Average number 2. Average length 5.2 mm. Edges — doubly serrate. Color 5GY 4/8.

*Color*.—Upper surface 10Y 3/2 to 10Y 2/2. Lower surface varies from 7.5Y 4/4 to 10Y 4/2. Midvein color varies from 10Y 7/4 to 2.5GY 6/6.

Flower buds:

*Size*.—Small to medium. Average length 9.1 mm. Average diameter 5.0 mm.

*Hardiness*.—Hardy with respect to California winters.

*Form*.—Conical, becoming elongated just before opening.

*Pedicel*.—Average length 5.8 mm. Average width 0.7 mm. Color varies from 2.5GY 8/6 to 2.5GY 7/8. Surface — glabrous.

*Color*.—N 9.5/(white).

*Number of buds per spur*.—Varies from 6 to 12, average number 9. Varies with age of spur.

Flowers:

*Blooming period*.—Date of First Bloom Feb. 19, 2014. Date of Petal Fall Mar. 1, 2014, varies slightly with climatic conditions.

*Size*.—Medium to large. Average height 10.4 mm. Average diameter 19.5 mm.

*Petals*.—Normally 5, alternately arranged to sepals. Size — small to medium. Average length 9.9 mm. Average width 7.2 mm. Form — elliptical. Apex — rounded. Base — rounded to somewhat truncated. Arrangement — free. Margin — sinuate. Color N 9.5/(white). Both upper and lower surfaces glabrous.

*Sepals*.—Normally 5, alternately arranged to petals. Size — small. Average length 2.4 mm. Average width 2.6 mm. Shape — triangular. Apex rounded. Margin — entire. Both upper and lower surfaces glabrous. Color — upper surface varies from 2.5GY 7/6 to 2.5GY 6/6. Lower surface varies from 2.5GY 6/6 to 5GY 7/6.

*Stamens*.—Average number per flower 29. Average filament length 7.1 mm. On average, the stamens are even with the height of the petals. Filament color N 9.5/(white). Anther color varies from 5Y 8/8 to 5Y 7/10.

*Pollen*.—Self-sterile, pollinator required. Color varies from 2.5Y 7/10 to 5Y 7/10.

*Pistil*.—Number — normally 1. Average length 7.3 mm. Positions of stigma an average of 1.5 mm below anthers. Surface — glabrous. Color varies from 10Y 8.5/4 to 10Y 7/6.

*Fragrance*.—Heavy aroma.

*Color*.—N 9.5/(white).

*Pedicel*.—Average length 11.2 mm. Average width 0.7 mm. Color varies from 2.5GY 7/8 to 2.5GY 6/6. Surface — glabrous.

*Number flowers per flower bud*.—Average 4, varies from 2 to 5.

Fruit:

*Maturity when described*.—Firm ripe and ready for consumption.

*Date of first picking*.—Jul. 11, 2014.

*Date of last picking*.—Jul. 21, 2014, varies slightly with climatic conditions.

*Size*.—Medium to large. Average diameter axially 59.2 mm. Average transversely in suture plane 64.8 mm. Average weight 161.9 grams, varies slightly with fertility of the soil, amount of thinning and climatic conditions.

*Form*.—Globose.

*Suture*.—Smooth to very slightly lipped, extends from base to apex.

*Ventral surface*.—Nearly smooth.

*Apex*.—Slightly retuse.

*Base*.—Slightly retuse.

*Stem cavity*.—Rounded to slightly elongated in suture plane. Average depth 5.2 mm. Average diameter 9.1 mm.

Stem:

*Size*.—Medium. Average length 13.0 mm. Average diameter 2.8 mm.

*Color*.—Varies from 7.5YR 3/4 to 10YR 3/6.

Skin:

*Thickness*.—Medium.

*Surface*.—Smooth.

*Bloom*.—Moderate amount, completely covered.

*Tendency to crack*.—Very slight.

*Color*.—Ground color varies from 5Y 6/6 to 7.5Y 8/6. Overspread with 5R 4/6 to 7.5R 3/6. Small, randomly spaced areas of exposed ground color giving a speckling pattern to the surface.

*Tenacity*.—Tenacious to flesh.

*Astringency*.—Undetected.

Flesh:

*Ripens*.—Evenly.

*Texture*.—Firm, meaty.

*Fibers*.—Few, small, tender.

*Firmness*.—Firm, having good handling and shipping quality.

*Aroma*.—Moderate.

*Amydgalin*.—Undetected.

*Eating quality*.—Very good.

*Flavor*.—Very good, a good balance between acid and sugar.

*Juice*.—Heavy amount, enhances flavor.

*Acidity*.—Not available.

*Brix*.—Average Brix 17.6°, varies slightly with amount of fruit per tree and climatic conditions.

*Color*.—Varies from 2.5Y 8/4 to 5Y 8/6.

*Pit cavity*.—Average length 29.3 mm. Average width 22.4 mm. Average depth 6.0 mm. Color 2.5Y 7/6 to 5Y 7/6.

Stone:

*Type*.—Clingstone, strong adherence to flesh.

*Size*.—Medium to large. Average length 28.3 mm. Average width 21.4 mm. Average thickness 11.2 mm.

*Form*.—Obovoid.

*Base*.—Flat.

*Apex*.—Slightly pointed. Average length 0.5 mm.

*Surface*.—Slightly pitted throughout. One shallow groove on each side of suture extending from base to apex.

*Sides*.—Unequal, one side extending further outward from suture plane.

*Ridges*.—Very small, extending from base toward apex.

*Tendency to split*.—None.

*Color*.—Varies from 10YR 6/6 to 10YR 5/8 when dry.

Kernel:

*Size*.—Medium. Average length 15.5 mm. Average width 11.1 mm. Average depth 6.5 mm.

*Form*.—Ovoid.

*Viability*.—Viable, complete embryo development.

*Skin color*.—Varies from 5Y 9/4 to 7.5Y 9/4.

Use: Dessert.

*Market*.—Local and long distance.

Keeping quality: Good, held firm 3 weeks at 38° to 42° F. without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

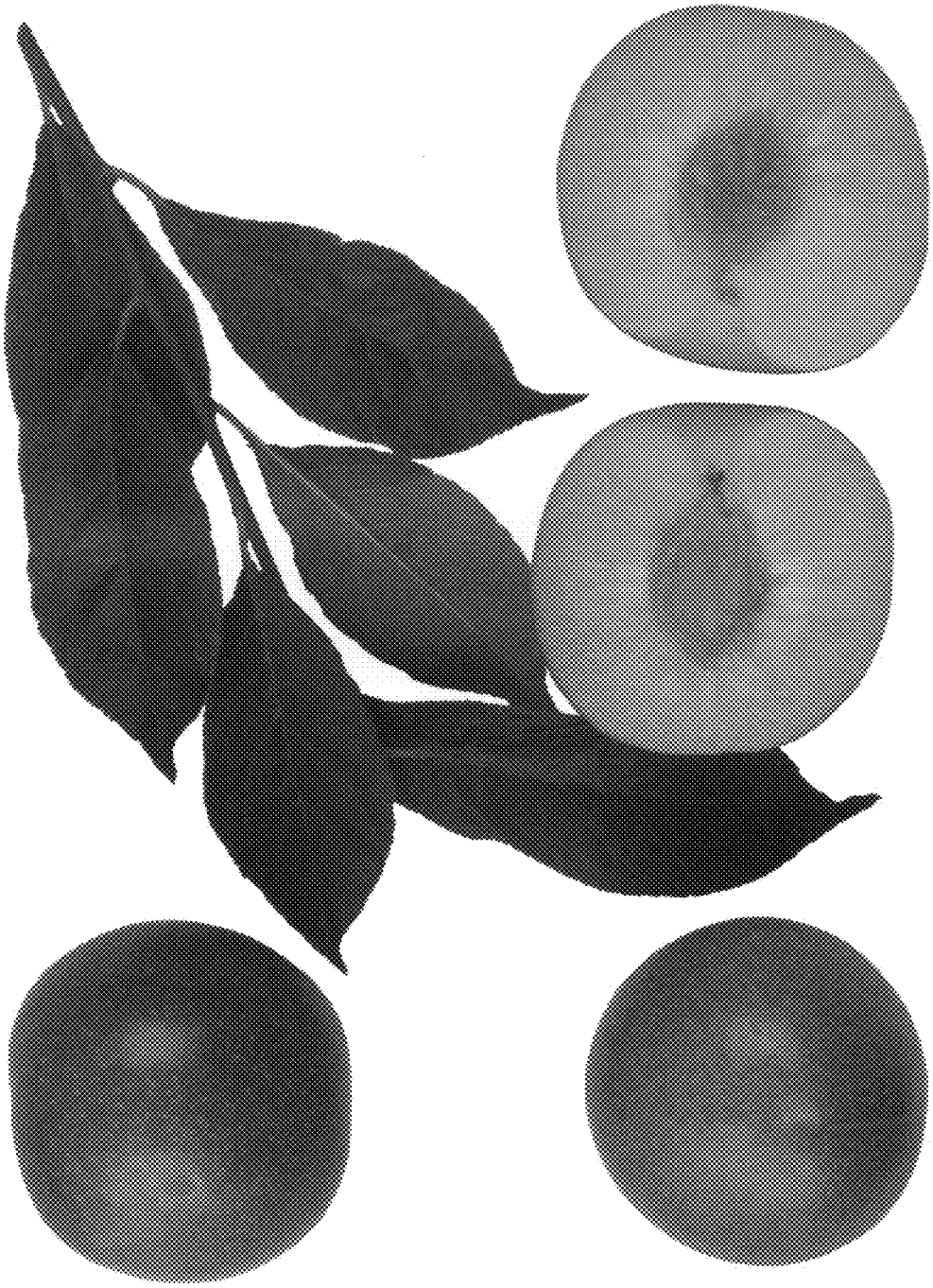

* * * * *